(12) United States Patent
Kluttz et al.

(10) Patent No.: US 10,159,783 B2
(45) Date of Patent: Dec. 25, 2018

(54) TWO-SIDED FLEXIBLE CLIP ASSEMBLY

(71) Applicants: Jason Kluttz, Vacaville, CA (US);
Cynthia Giaquinto, Vacaville, CA (US)

(72) Inventors: Jason Kluttz, Vacaville, CA (US);
Cynthia Giaquinto, Vacaville, CA (US)

(*) Notice: Subject to any disclaimer, the term of this patent is extended or adjusted under 35 U.S.C. 154(b) by 214 days.

(21) Appl. No.: 14/657,512

(22) Filed: Mar. 13, 2015

(65) Prior Publication Data

US 2015/0306305 A1    Oct. 29, 2015

Related U.S. Application Data

(60) Provisional application No. 61/985,243, filed on Apr. 28, 2014.

(51) Int. Cl.
| | | |
|---|---|---|
| *F21V 21/088* | (2006.01) | |
| *A61M 5/14* | (2006.01) | |
| *F16B 2/24* | (2006.01) | |

(52) U.S. Cl.
CPC ........ *A61M 5/1418* (2013.01); *A61M 5/1415* (2013.01); *F16B 2/24* (2013.01); *F16B 2/245* (2013.01)

(58) Field of Classification Search
CPC ..... F21V 21/08; F21V 21/088; A61M 5/1418; F16B 2/22; F16B 2/24; F16B 2/245
USPC ..... 248/219.4, 219.2, 218.4, 229.16, 229.26, 248/227.3, 228.7, 230.7, 231.81
See application file for complete search history.

(56) References Cited

U.S. PATENT DOCUMENTS

| | | | | |
|---|---|---|---|---|
| 1,268,622 | A * | 6/1918 | Reynolds | F21V 21/08 248/229.26 |
| 1,774,775 | A * | 9/1930 | Weitz, Jr. | F21L 15/08 248/229.26 |
| 3,216,687 | A * | 11/1965 | Vardan | A61J 9/06 248/103 |
| 3,318,457 | A * | 5/1967 | Krasnoff | A61M 5/1415 211/74 |
| 3,370,820 | A * | 2/1968 | Liss | A24F 19/0092 131/241 |
| 3,468,428 | A * | 9/1969 | Reibold | A47F 5/06 108/103 |
| 3,604,687 | A * | 9/1971 | Moore | E04H 17/1413 256/65.03 |
| 3,747,166 | A * | 7/1973 | Eross | F16L 3/085 248/229.26 |

(Continued)

*Primary Examiner* — Nkeisha Smith

(57) ABSTRACT

A device for holding an intravenous (IV) pole and a drip chamber/filter in parallel to each other includes a first clip member and a second clip member. The first clip member and the second clip member are positioned coplanar to each other. Moreover, the first clip member is connected to the second clip member. The first clip member is made of a first base section, a first left prong, a first right prong, and a first opening. Similarly, the second clip member is made of a second base section, a second left prong, a second right prong, and a second opening. If the IV pole is positioned within the first opening, the drip chamber/filter is positioned within the second opening. In order to eliminate slipping, a slip resistant coating is externally layered onto the first left prong, the first right prong, the second left prong, and the second right prong.

10 Claims, 9 Drawing Sheets

(56) References Cited

U.S. PATENT DOCUMENTS

| | | | | |
|---|---|---|---|---|
| 4,040,547 A * | 8/1977 | Dickey | F16M 13/04 | 224/247 |
| 4,115,966 A * | 9/1978 | DeLee | G09F 7/18 | 248/229.26 |
| 4,213,649 A * | 7/1980 | Sell | A47C 7/62 | 248/231.81 |
| 4,688,961 A * | 8/1987 | Shioda | F16B 7/04 | 24/336 |
| 5,137,243 A * | 8/1992 | Stevens | A47G 25/12 | 248/316.7 |
| 5,188,327 A * | 2/1993 | White | F16B 12/54 | 248/231.81 |
| 5,288,047 A * | 2/1994 | Pan | F16L 3/237 | 248/229.26 |
| 5,443,232 A * | 8/1995 | Kesinger | H02G 3/263 | 248/62 |
| 5,697,129 A * | 12/1997 | Newville | B25F 1/02 | 24/339 |
| 5,794,898 A * | 8/1998 | Bradley | A61J 9/06 | 248/102 |
| 7,293,745 B2 * | 11/2007 | Catapano | H02G 3/30 | 248/61 |
| 8,777,170 B2 * | 7/2014 | Gilbert | A63H 3/50 | 224/666 |
| 2005/0098695 A1 * | 5/2005 | Hollenbeck | A61H 3/0244 | 248/229.26 |
| 2010/0012804 A1 * | 1/2010 | Egan | F16B 9/023 | 248/231.81 |
| 2014/0173888 A1 * | 6/2014 | Reiter | A61B 8/0891 | 29/594 |
| 2015/0211678 A1 * | 7/2015 | Bulka | F16M 13/022 | 248/229.16 |

* cited by examiner

TWO-SIDED FLEXIBLE CLIP ASSEMBLY

The current application claims a priority to the U.S. Provisional Patent application Ser. No. 61/985,243 filed on Apr. 28, 2014.

FIELD OF THE INVENTION

The present invention relates generally to a clip for maintaining two objects in a vertical and parallel arrangement. More specifically, the present invention is a dual-sided clip for maintaining an intravenous (IV) therapy pole and an IV drip chamber/filter in a vertical and parallel arrangement.

BACKGROUND OF THE INVENTION

Intravenous (IV) therapy is utilized for a wide variety of applications including the replacement of fluids, the delivery of medications, and blood transfusions, among others. IVs are generally administered by bags of fluid that are already premixed prior to administration. During IV therapy, the IV bag is securely hung from an IV pole with IV tubing components attached to the bottom of the bag. IV tubing typically comprises a drip chamber/filter that is located directly below the IV bag. The drip chamber/filter serves as a conduit through which fluid drips down from the IV bag and is often clear in order to facilitate observation when determining drip rate. When administering fluids via IV therapy, it is common to utilize a filter prior to infusion into the patient in order to ensure that air and particulate matter is unable to pass through the filter while fluids are able to pass. A hydrophilic filter is often included within the drip chamber/filter with the filter constantly wetted as the fluid within the IV bag drips onto the filter. In order for the filter to be effective, the entire surface area of the filter must be covered with fluid. However, this is at times difficult as the cylindrical drip chamber/filter often does not remain vertical and parallel relative to the IV pole during IV administration. This is due to the fact that the drip chamber/filter is often free-hanging from the bottom of the IV bag with no structural support in place. A non-parallel configuration can be problematic during IV administration, particularly when performing a blood transfusion. During a blood transfusion, blood that drips into a drip chamber/filter that is not parallel to the IV pole tends to hit the side wall of the drip chamber/filter and cause the blood cells to rupture and be rendered useless (Hemolysis). If the filter is left uncovered, air and particulate matter can travel through the filter into the tubing and reach the patient. The present invention seeks to address the aforementioned issues as well as provide a practical, functional, and convenient solution.

The present invention is a dual-sided clip for holding an IV pole and an IV drip chamber/filter vertical and parallel relative to one another. In the preferred embodiment of the present invention, the dual-sided clip comprises a first clip member and a second clip member. The first clip member and the second clip member are identical in terms of design. Each clip member comprises a single-piece, approximately U-shaped member of uniform thickness. Each U-shaped clip member further comprises a left prong, a right prong, and a central connector portion. The interior portions of the left prong and the right prong are rounded in order to accommodate a cylindrical structure such as an IV pole and a drip chamber/filter between the left prong and right prong. Each clip member is composed of a flexible material that allows the insertion of a cylindrical structure between the left prong and right prong and that secures the clip member in place on the cylindrical structure once attached. In the preferred embodiment of the present invention, the surfaces of the interior portions of the left prong and right prong are covered with a slip resistant coating in order to maintain a secure grip on a cylindrical structure inserted between the left prong and right prong.

The dual-sided clip is available in a single piece configuration as well as a multi-piece assembled configuration. In the single piece configuration, the dual-sided clip first clip member and second clip member are positioned back-to-back with the exterior surfaces of the central connector portions positioned together. The clip member prongs are positioned facing in opposite directions. Unlike the single-piece configuration, the clip members are independent of one another in the multi-piece configuration. In the multi-piece assembled configuration, the dual-sided clip first clip member and second clip member are positioned back-to-back, similar to the single piece configuration. The individual clip members are secured together utilizing fasteners such as screws. In both the single piece configuration and the multi-piece assembled configuration, the first clip member and second clip member are oriented in a manner such that a cylindrical IV pole and a cylindrical drip chamber/filter inserted into the first clip member and the second clip member are maintained vertical and parallel to one another.

DETAIL DESCRIPTIONS OF THE INVENTION

All illustrations of the drawings are for the purpose of describing selected versions of the present invention and are not intended to limit the scope of the present invention.

The present invention is a device utilized to maintain an intravenous (IV) pole and a drip chamber/filter vertical and parallel to one another. A vertical position is essential for the drip chamber/filter during IV therapy. If the drip chamber/filter used during IV therapy is not vertical, the blood within the drip chamber/filter tends to hit the interior walls of the drip chamber/filter, which lessens the quality of the blood that is transfused. By utilizing the present invention, the blood being transfused to the patient maintains the intended quality.

As seen in FIGS. 1-4, the present invention comprises a first clip member 1 and a second clip member 8. The first clip member 1 and the second clip member 8 are utilized to hold the IV pole and the drip chamber/filter in parallel when the present invention is in use. In order to do so, the first clip member 1 is adjacently connected to the second clip member 8. As a result, the IV pole and the drip chamber/filter are positioned parallel to each other at a distance specified by the first clip member 1 and the second clip member 8. Moreover, the first clip member 1 is positioned coplanar to the second clip member 8 allowing the user to conveniently attach the IV pole and the drip chamber/filter to the first clip member 1 and the second clip member 8.

Figure 1:
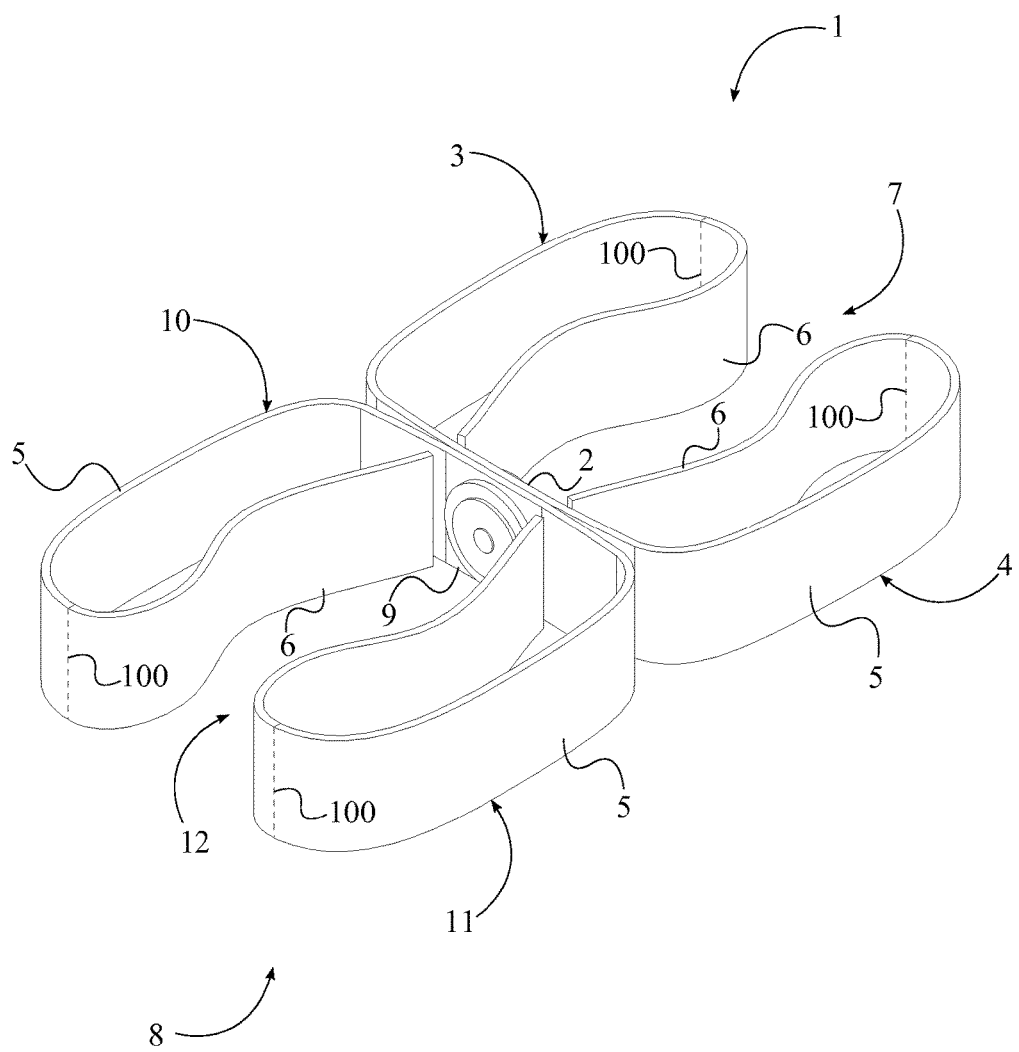
FIG. 1 is an isometric view of the present invention, wherein a first clip member and a second clip member are connected to each other with an attachment mechanism.
Figure 2:
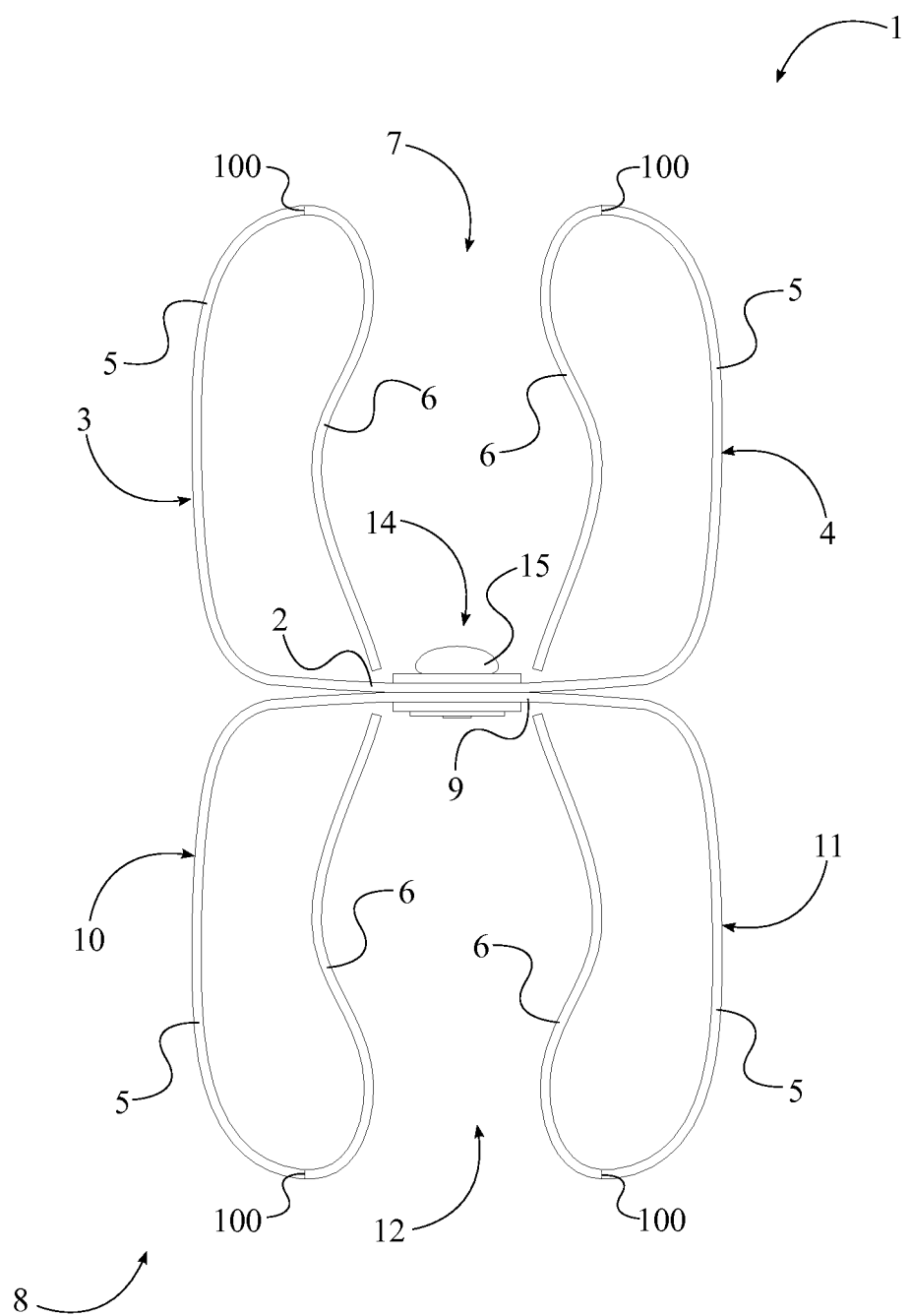
FIG. 2 is a top view of present invention, wherein the first clip member and the second clip member are connected to each other with the attachment mechanism.
Figure 4:
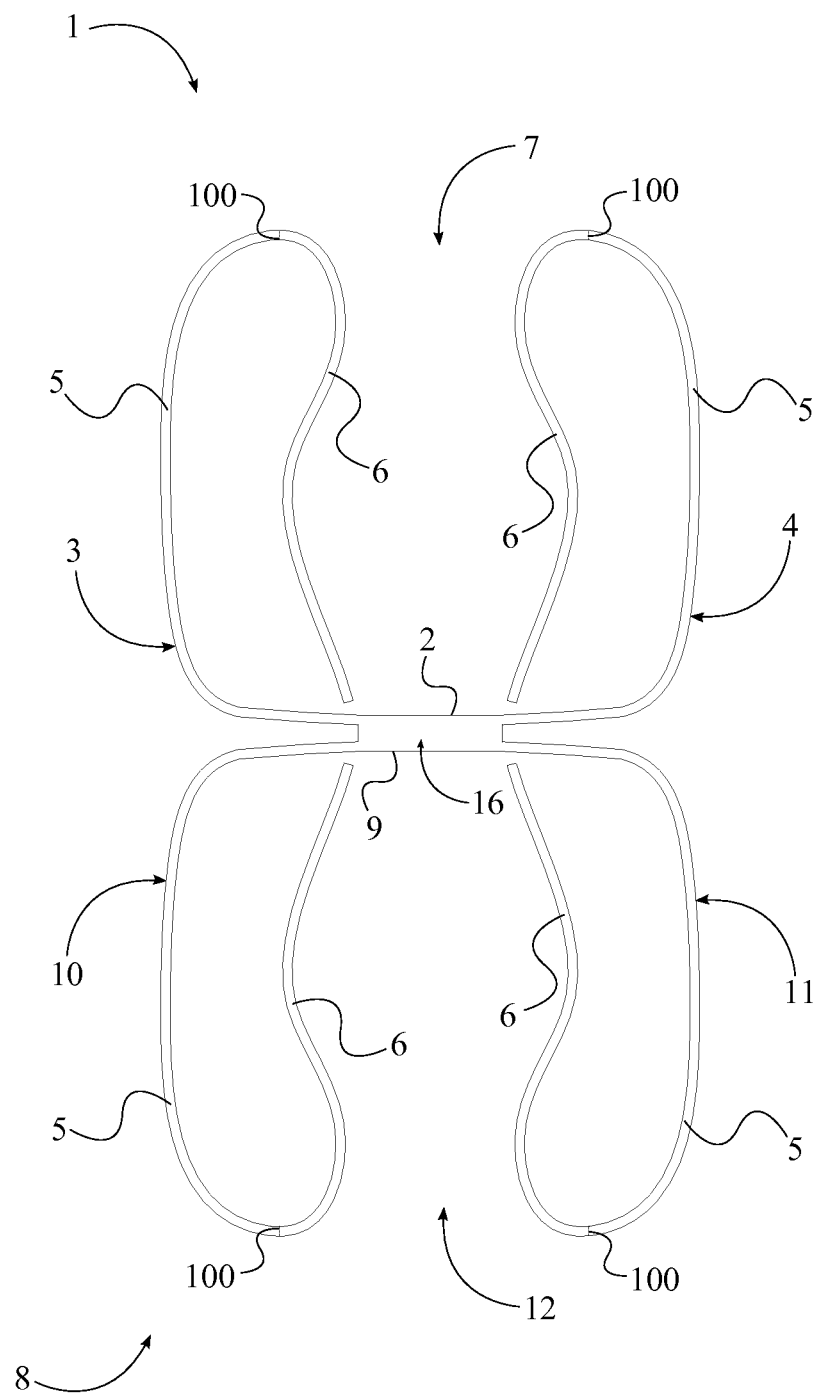
FIG. 4 is a top view of the present invention, wherein the first clip member and the second clip member are connected to each other with the securing block.
Figure 5:
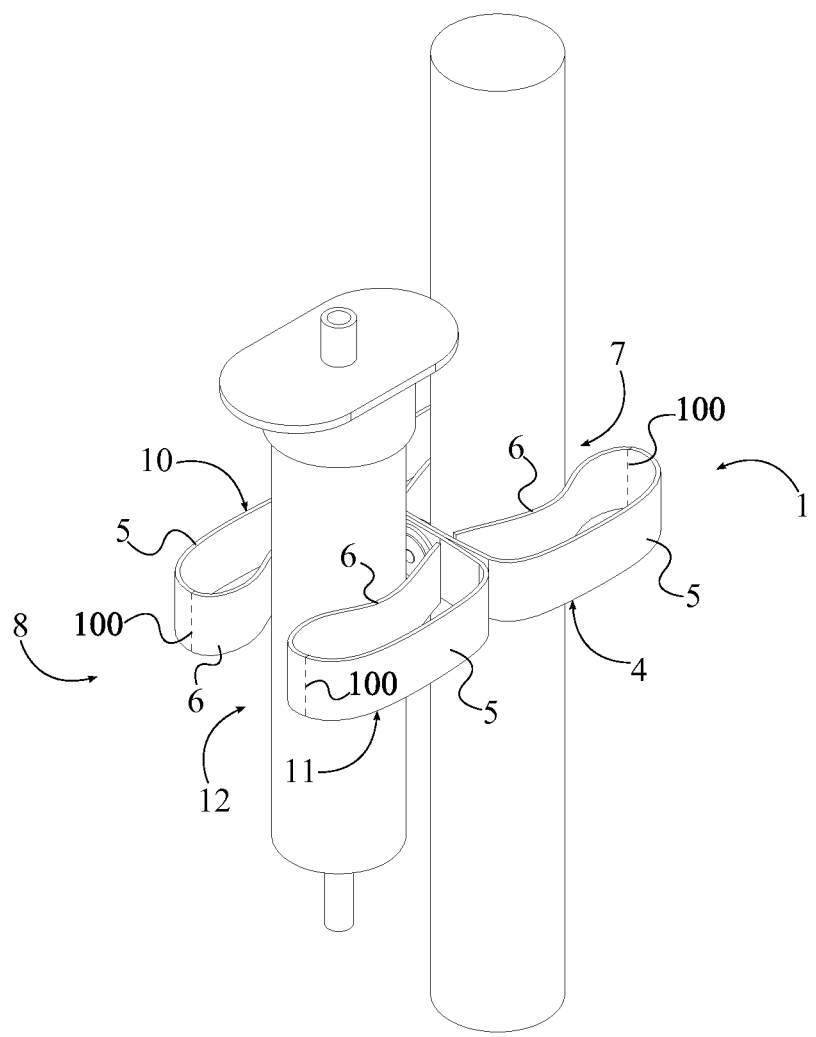
FIG. 5 is an isometric view of the present invention, wherein an IV pole is inserted into the first clip member and a drip chamber/filter is inserted into the second clip member.
Figure 6:
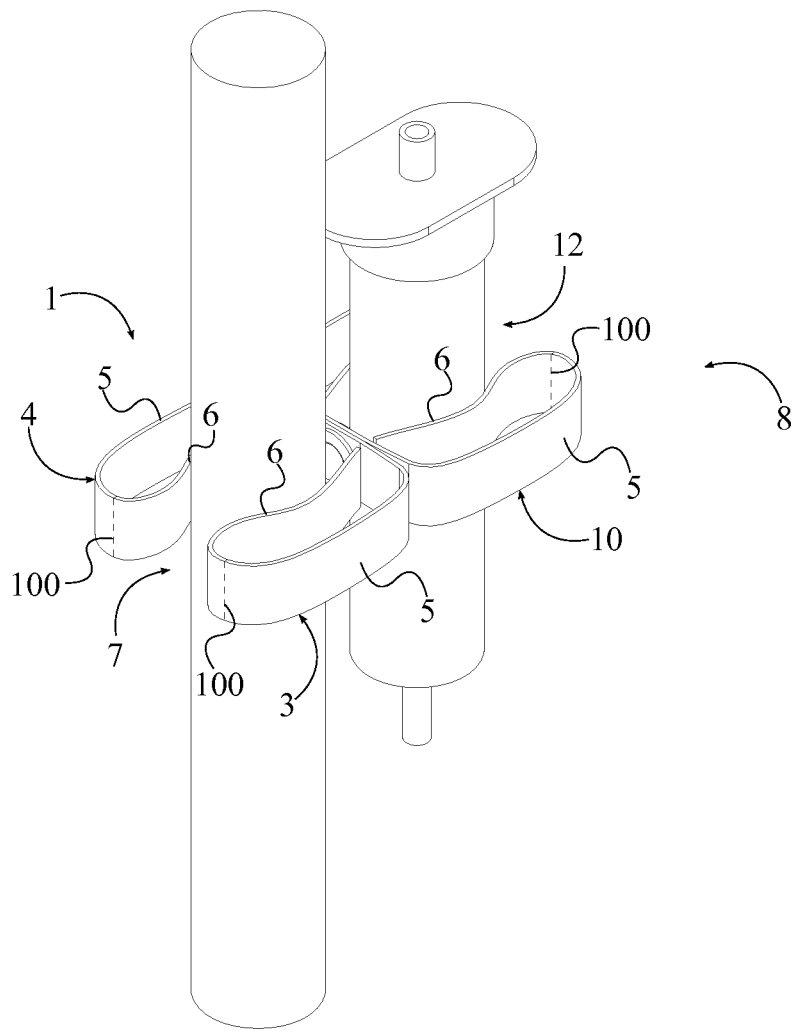
FIG. 6 is an alternate isometric view of the present invention, wherein the IV pole is inserted into the first clip member and the drip chamber/filter is inserted into the second clip member.
Figure 7:
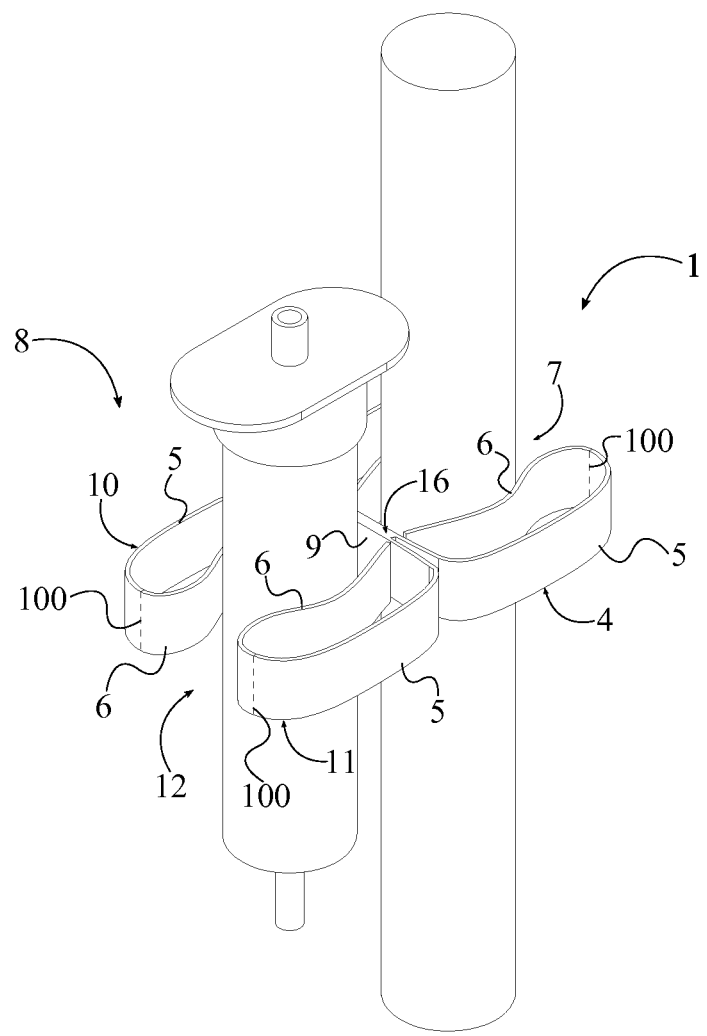
FIG. 7 is an isometric view of the present invention, wherein the IV pole is inserted into the first clip member and the drip chamber/filter is inserted into the second clip member when the first clip member and the second clip member are connected with the securing block.
Figure 8:
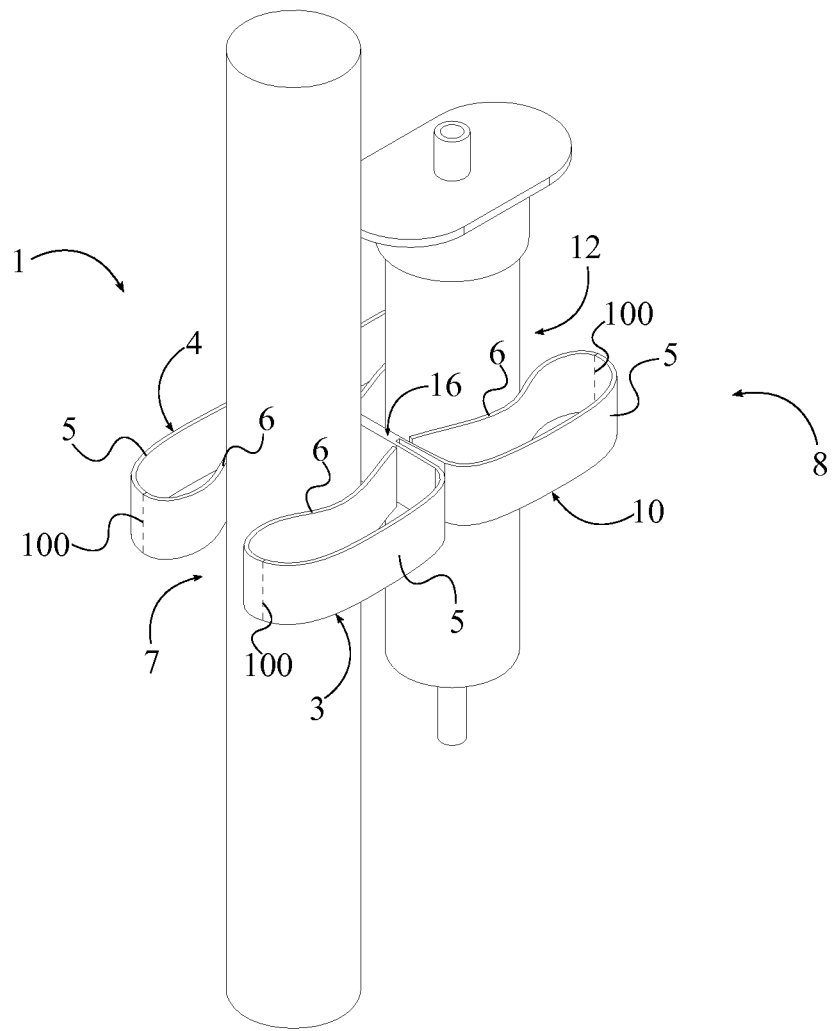
FIG. 8 is an alternate isometric view of the present invention, wherein the IV pole is inserted into the first clip member and the drip chamber/filter is inserted into the second clip member when the first clip member and the second clip member are connected with the securing block.

As shown in FIG. 2 and FIG. 4, the first clip member 1 and the second clip member 8 are designed to securely position the IV pole and the drip chamber/filter. In order to secure the IV pole or the drip chamber/filter, the first clip member 1 comprises a first base section 2, a first left prong 3, a first right prong 4, and a first opening 7. The first clip member 1 forms a U-shaped body in the preferred embodiment of the present invention. In order to structure the U-shaped body, the first left prong 3 and the first right prong 4 are connected to the first base section 2. More specifically, the first left prong 3 and the first right prong 4 are positioned opposite of each other along the first base section 2. If the IV pole is vertically positioned within the first clip member 1, the IV pole is secured with the first left prong 3 and the first right prong 4. The first opening 7 is positioned in between the first left prong 3 and the first right prong 4. Therefore, when the IV pole is secured between the first left prong 3 and the first right prong 4, the IV pole is positioned within the first opening 7. The first opening 7 is delineated by the first left prong 3, the first right prong 4, and the first base section 2. Resultantly, when the IV pole is positioned within the first opening 7, the IV pole is also adjacent to the first base section 2 and positioned in between the first left prong 3 and the first right prong 4.

Similar to the first clip member 1, the second clip member 8 comprises a second base section 9, a second left prong 10, a second right prong 11, and a second opening 12. Similar to the first clip member 1, the second clip member 8 also forms a U-shaped body in the preferred embodiment of the present invention. In order to structure the U-shaped body, the second left prong 10 and the second right prong 11 are connected to the second base section 9. In particular, the second left prong 10 and the second right prong 11 are positioned opposite of each other along the second base section 9. If the IV pole is initially positioned within the first clip member 1, the drip chamber/filter is positioned within the second opening 12 vertical and parallel to the IV pole. The second opening 12 is positioned in between the second left prong 10 and the second right prong 11. Furthermore, the second opening 12 is delineated by the second left prong 10, the second right prong 11 and the second base section 9. As a result, the drip chamber/filter is positioned in between the second left prong 10 and the second right prong 11 and also positioned adjacent to the second base section 9. According to user preference, the drip chamber/filter can also be positioned within the first clip member 1 and the IV pole can be positioned within the second clip member 8.

As seen in FIG. 1-4, the first clip member 1 is identical to the second clip member 8. The first left prong 3, the first right prong 4, the second left prong 10, and the second right prong 11 each comprise an outer arm section 5 and an inner arm section 6. When the IV pole is inserted into the first clip member 1, the IV pole is in contact with the inner arm section 6 of both the first left prong 3 and the first right prong 4. In the preferred embodiment of the present invention, the inner arm section 6 has a rounded edge such that the IV pole or the drip chamber/filter is securely positioned within the first clip member 1 or the second clip member 8. The rounded edge corresponds to the cylindrical shape of the IV pole or the drip chamber/filter. The inner arm section 6 is adjacently connected to the outer arm section 5 along a connector line 100, allowing the user to control the position of the inner arm section 6 by manipulating the outer arm section 5. When considering the first clip member 1, the first base section 2 is adjacently connected to the outer arm section 5 of the first left prong 3 opposite the connector line 100 of the first left prong 3. Likewise, the first base section 2 is adjacently connected to the outer arm section 5 of the first right prong 4 opposite the connector line 100 of the first right prong 4. Therefore, the outer arm section 5 of the first left prong 3 and the outer arm section 5 of the first right prong 4 are positioned on opposite sides of the first base section 2. The positioning of the outer arm section 5 allows the user to control the first right prong 4 independent of the first left prong 3. Moreover, the inner arm section 6 and the outer arm section 5 of the first left prong 3 and the first right prong 4 are flexible such that the user can control the first opening 7 conveniently.

As illustrated in FIGS. 5-8, if the IV pole is positioned within the first opening 7, then the drip chamber/filter is positioned within the second opening 12. When the drip chamber/filter is positioned within the second opening 12, the drip chamber/filter is in contact with the inner arm section 6 of the second left prong 10 and the second right prong 11. Similar to the first base section 2, the second base section 9 is adjacently connected to the outer arm section 5 of the second left prong 10 opposite the connector line 100 of the second left prong 10. Moreover, the second base section 9 is adjacently connected to the outer arm section 5 of the second right prong 11 opposite the connector line 100 of the second right prong 11. As a result, the outer arm section 5 of the second left prong 10 and the outer arm section 5 of the second right prong 11 are on either side of the second base section 9. The positioning of the outer arm section 5 of the second left prong 10 and the second right prong 11 allows the user to control the second left prong 10 independent of the second right prong 11 or vice versa. The inner arm section 6 and the outer arm section 5 of the second left prong 10 and the second right prong 11 are also flexible. The flexibility allows the user to control the second opening 12 conveniently.

Figure 9:
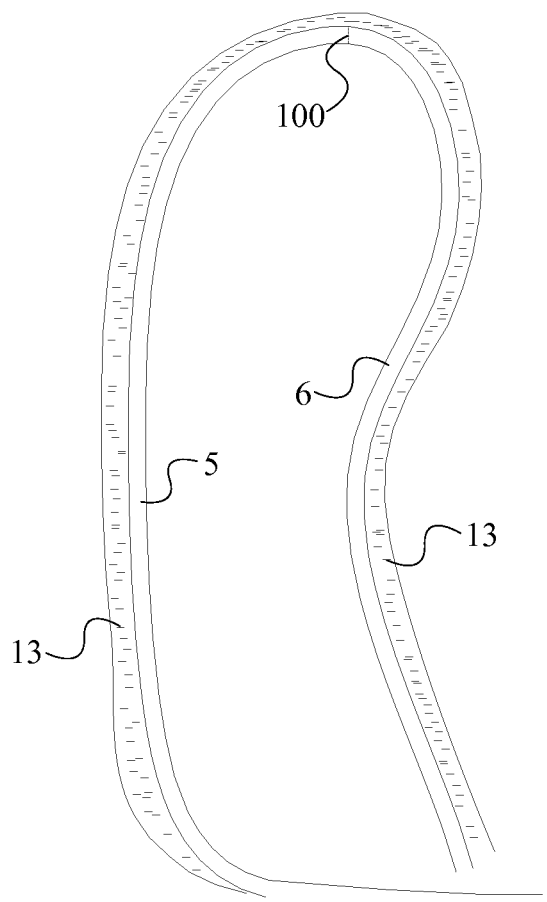
FIG. 9 is a top view illustrating a slip resistant coating being externally layered in the present invention.

As discussed earlier, when the IV pole is positioned within the first opening 7, the inner arm section 6 of both the first left prong 3 and the first right prong 4 are in contact with the IV pole. Similarly, when the drip chamber/filter is positioned within the second opening 12, the inner arm section 6 of both the second left prong 10 and the second right prong 11 are in contact with the drip chamber/filter. However, if the points of contact for the IV pole and the drip chamber/filter are overly smooth, the present invention tends to slide along the IV pole and the drip chamber/filter. In order to prevent sliding, the present invention comprises a slip resistant coating 13. The slip resistant coating 13 is externally layered onto the first left prong 3 and the first right prong 4 in order to secure the IV pole in place. Similarly, the slip resistant coating 13 also externally applied onto the second left prong 10 and the second right prong 11 such that the drip chamber/filter remains stationary within the second opening 12. FIG. 9 is an illustration of the slip resistant coating 13 being externally layered on the present invention.

As discussed earlier, the first clip member 1 is adjacently connected to the second clip member 8. More specifically, the first base section 2 is attached to the second base section 9. In the preferred embodiment of the present invention, an attachment mechanism 14 is utilized to attach the first clip member 1 to the second clip member 8. As seen in FIG. 2, the first base section 2 is attached to the second base section 9 with the attachment mechanism 14. When the first base section 2 and the second base section 9 are attached together, an at least one fastener 15 of the attachment mechanism 14 traverses through the first base section 2 and the second base section 9. However, in another embodiment a different attachment mechanism can also be utilized.

Figure 3:
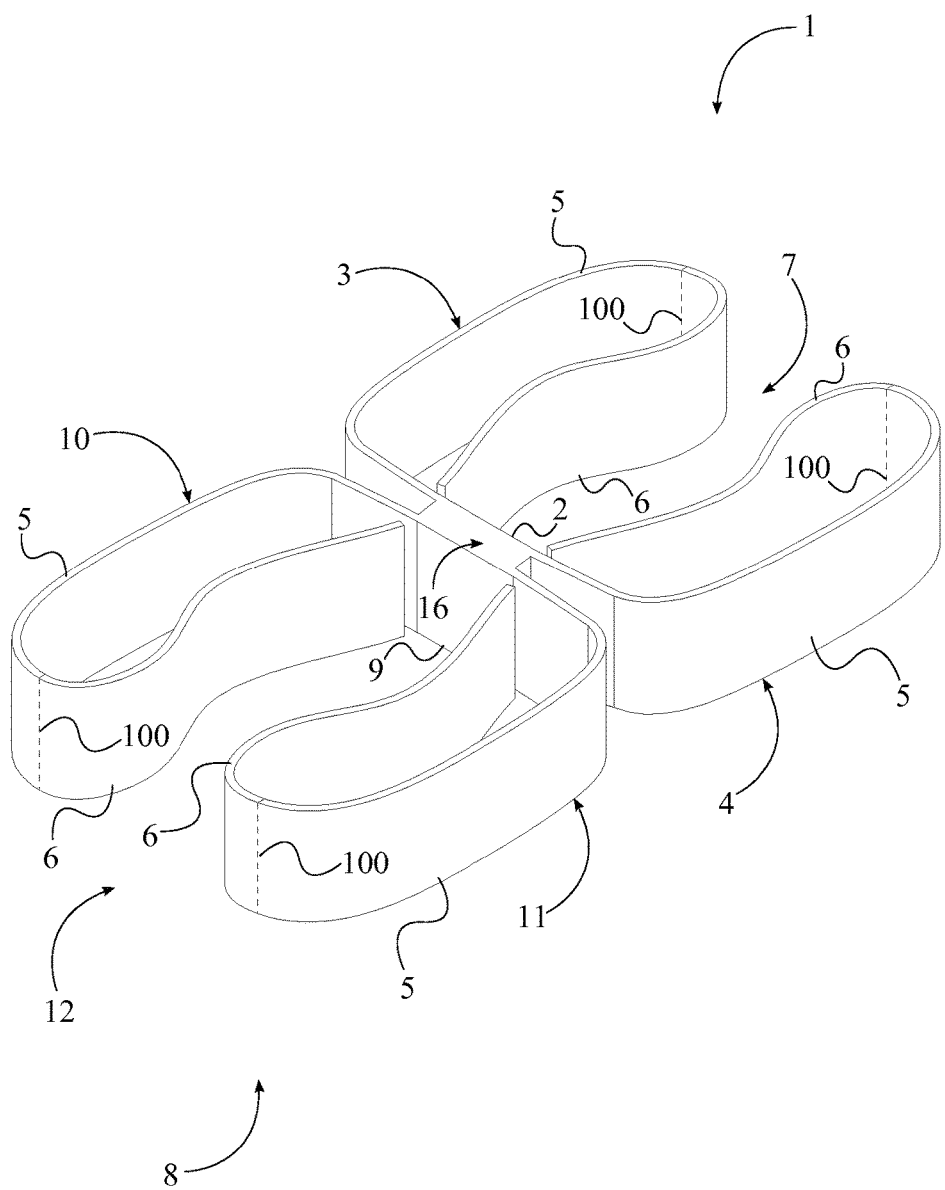
FIG. 3 is an isometric view of the present invention, wherein the first clip member and the second clip member are connected to each other with a securing block.

In another embodiment of the present invention, the first clip member 1 is fixed to the second clip member 8 as illustrated in FIG. 3 and FIG. 4. A securing block 16 is utilized in order to connect the first clip member 1 to the second clip member 8. More specifically, the first base section 2 is connected to the second base section 9 with the securing block 16.

In order to provide convenience to the user, the present invention can be made of materials which can be, but is not limited to, spring steel or lightweight plastic. The flexibility provided through these materials is essential when placing the IV pole and the drip chamber/filter within the first clip member 1 and the second clip member 8 respectively. Furthermore, the present invention can also be created to be disposable and reusable in different embodiments of the present invention.

Even though the flexibility of the first clip member 1 and the second clip member 8 are utilized in the preferred embodiment of the present invention, a spring mechanism can be utilized in another embodiment of the present invention. In such instances, the spring mechanism is integrated into the first clip member 1 and the second clip member 8. Therefore, the user can utilize the spring mechanism of the first clip member 1 to control the first left prong 3 and the first right prong 4. Similarly, the user can utilize the spring mechanism of the second clip member 8 to control the second left prong 10 and the second right prong 11.

In utilizing the present invention, the subsequent process flow is followed. For instance, consider positioning the IV pole within the first clip member 1. As a primary step, the user controls the first left prong 3 and the first right prong 4 in order to position the IV pole within the first opening 7. The rounded edge of both the first left prong 3 and the first right prong 4 aids in keeping the IV pole stationary within the first clip member 1. Similarly, the drip chamber/filter is positioned within the second opening 12 by controlling the second left prong 10 and the second right prong 11. The rounded edge of both the second left prong 10 and the second right prong 11 aids in keeping the drip chamber/filter stationary within the second opening 12. Additionally, the slip resistant coating 13 also helps in keeping the IV pole and the drip chamber/filter stationary. When the IV pole and the drip chamber/filter are inserted into the first opening 7 and the second opening 12 respectively, the user positions the present invention at a desired height by sliding the present invention along the IV pole.

Although the invention has been explained in relation to its preferred embodiment, it is to be understood that many other possible modifications and variations can be made without departing from the spirit and scope of the invention as hereinafter claimed.

What is claimed is:

1. An apparatus for holding an intravenous pole and a drip chamber/filter in parallel to each other comprises:
    a first clip member;
    a second clip member;
    the first clip member comprises a first base section, a first left prong, a first right prong, and a first opening;
    the second clip member comprises a second base section, a second left prong, a second right prong, and a second opening;
    the first opening being delineated by the first left prong, the first right prong, and the first base section;
    the second opening being delineated by the second left prong, the second right prong, and the second base section;
    the first clip member being positioned coplanar to the second clip member;
    the first clip member being adjacently connected to the second clip member;
    the first left prong and the first right prong being connected to the first base section;
    the first left prong and the first right prong being positioned opposite of each other along the first base section;
    the first opening being positioned in between the first left prong and the first right prong;
    the first left prong, the first right prong, the second left prong, and the second right prong each comprise an outer arm section and an inner arm section;
    the inner arm section being adjacently connected to the outer arm section along a connector line;
    the first base section being adjacently connected to the outer arm section of the first left prong opposite the connector line of the first left prong;
    the first base section being adjacently connected to the outer arm section of the first right prong opposite the connector line of the first right prong;
    the second base section being adjacently connected to the outer arm section of the second left prong opposite the connector line of the second left prong;
    the second base section being adjacently connected to the outer arm section of the second right prong opposite the connector line of the second right prong;
    the first clip member and the second clip member each form a U-shaped body;
    the first clip member and the second clip member are made with spring steel;
    a slip resistant coating;
    the slip resistant coating being externally layered onto the first left prong and the first right prong; and
    the slip resistant coating being externally layered onto the second left prong and the second right prong.

2. The apparatus for holding an intravenous pole and a drip chamber/filter in parallel to each other as claimed in claim 1 comprises:
    the second left prong and the second right prong being connected to the second base section;
    the second left prong and the second right prong being positioned opposite of each other along the second base section; and
    the second opening being positioned in between the second left prong and the second right prong.

3. The apparatus for holding an intravenous pole and a drip chamber/filter in parallel to each other as claimed in claim 1 comprises:
   an attachment mechanism; and
   the first base section being attached to the second base section with the attachment mechanism.

4. The apparatus for holding an intravenous pole and a drip chamber/filter in parallel to each other as claimed in claim 3 comprises:
   the attachment mechanism comprises an at least one fastener; and
   the at least one fastener traversing through the first base section and the second base section.

5. The apparatus for holding an intravenous pole and a drip chamber/filter in parallel to each other as claimed in claim 1 comprises:
   a securing block; and
   the first base section being connected to the second base section with the securing block.

6. An apparatus for holding an intravenous pole and a drip chamber/filter in parallel to each other comprises:
   a first clip member;
   a second clip member;
   the first clip member comprises a first base section, a first left prong, a first right prong, and a first opening;
   the second clip member comprises a second base section, a second left prong, a second right prong, and a second opening;
   the first opening being delineated by the first left prong, the first right prong, and the first base section;
   the second opening being delineated by the second left prong, the second right prong, and the second base section;
   the first clip member being positioned coplanar to the second clip member;
   the first clip member being adjacently connected to the second clip member;
   the first left prong and the first right prong being connected to the first base section;
   the first left prong and the first right prong being positioned opposite of each other along the first base section;
   the first opening being positioned in between the first left prong and the first right prong;
   an attachment;
   the attachment mechanism comprises an at least one fastener;
   the at least one fastener traversing through the first base section and the second base section;
   the first left prong, the first right prong, the second left prong, and the second right prong each comprise an outer arm section and an inner arm section;
   the inner arm section being adjacently connected to the outer arm section along a connector line;
   the first base section being adjacently connected to the outer arm section of the first left prong opposite the connector line of the first left prong;
   the first base section being adjacently connected to the outer arm section of the first right prong opposite the connector line of the first right prong;
   the second base section being adjacently connected to the outer arm section of the second left prong opposite the connector line of the second left prong;
   the second base section being adjacently connected to the outer arm section of the second right prong opposite the connector line of the second right prong;
   the second left prong and the second right prong being connected to the second base section;
   the second left prong and the second right prong being positioned opposite of each other along the second base section;
   the second opening being positioned in between the second left prong and the second right prong;
   a slip resistant coating;
   the slip resistant coating being externally layered onto the first left prong and the first right prong; and
   the slip resistant coating being externally layered onto the second left prong and the second right prong.

7. The apparatus for holding an intravenous pole and a drip chamber/filter in parallel to each other as claimed in claim 6 comprises:
   the first base section being attached to the second base section with the attachment mechanism.

8. The apparatus for holding an intravenous pole and a drip chamber/filter in parallel to each other as claimed in claim 6 comprises:
   a securing block; and
   the first base section being connected to the second base section with the securing block.

9. The apparatus for holding an intravenous pole and a drip chamber/filter in parallel to each other as claimed in claim 6, wherein the first clip member and the second clip member each form a U-shaped body.

10. The apparatus for holding an intravenous pole and a drip chamber/filter in parallel to each other as claimed in claim 6, wherein the first clip member and the second clip member are made with spring steel.

* * * * *